United States Patent
Koll et al.

(10) Patent No.: US 6,346,274 B1
(45) Date of Patent: *Feb. 12, 2002

(54) POLYPEPTIDE-CONTAINING PHARMACEUTICAL FORMS OF ADMINISTRATION IN THE FORM OF MICROPARTICLES AND METHOD FOR THE PREPARATION THEREOF

(75) Inventors: Hans Koll, Weilheim; Gerhard Winter, Dossenheim; Thomas Kissel, Marburg; Michael Morlock, Viernheim, all of (DE)

(73) Assignee: Roche Diagnostics GmbH, Mannheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/894,796
(22) PCT Filed: Mar. 7, 1996
(86) PCT No.: PCT/EP96/00980
    § 371 Date: Jan. 5, 1998
    § 102(e) Date: Jan. 5, 1998
(87) PCT Pub. No.: WO96/28143
    PCT Pub. Date: Sep. 19, 1996

(30) Foreign Application Priority Data

Mar. 10, 1995 (DE) .......................... 195 08 612
Apr. 11, 1995 (DE) .......................... 195 13 659
Nov. 17, 1995 (DE) .......................... 195 42 837

(51) Int. Cl.$^7$ .......................... A61K 9/16; A61K 47/34; A61K 47/36
(52) U.S. Cl. .......................... 424/497; 424/493
(58) Field of Search .......................... 424/489, 497, 424/491, 493, 426

(56) References Cited

U.S. PATENT DOCUMENTS 5,554,388 A * 9/1996 Illum
5,665,394 A * 9/1997 Igari et al.
5,690,954 A * 11/1997 Illum

* cited by examiner

Primary Examiner—Edward J. Webman
(74) Attorney, Agent, or Firm—Arent Fox Kintner Plotkin & Kahn, PLLC

(57) ABSTRACT

The invention concerns parenteral pharmaceutical forms of administration containing polypeptide in the form of microparticles and a process for the production thereof. The microparticles according to the invention contain as a biodegradable polymer an ABA triblock copolymer the A block of which is a copolymer of lactic and glycolic acid and the B block of which represents a polyethylene glycol chain, together with additives that are selected from the group comprising serum proteins, polyamino acids, cyclodextrins, cyclodextrin derivatives, saccharides, amino sugars, amino acids, detergents or carboxylic acids as well as mixtures of these additives. The microparticles according to the invention continuously release the polypeptide over a relatively long time period even when the amounts of polypeptide they include are small or susceptible to aggregation.

28 Claims, No Drawings

POLYPEPTIDE-CONTAINING PHARMACEUTICAL FORMS OF ADMINISTRATION IN THE FORM OF MICROPARTICLES AND METHOD FOR THE PREPARATION THEREOF

The present invention concerns parenteral pharmaceutical forms of administration in the form of microparticles (MP) for the controlled release of polypeptides and a process for the production of these microparticles.

As a result of the rapid advance of developments in biotechnology, numerous bioactive macromolecules are available in an adequate quantity for clinical application. Due to their structure they are hydrolytically cleaved in the gastro-intestinal tract and can therefore only be administered parenterally. Since they have a short half-life it is useful to develop parenteral depot systems in order to reduce the frequency of injections and to achieve a constant blood level.

A number of depot systems, in particular microparticulate systems, have been described in the technical and patent literature which release physiologically active substances after parenteral administration as constantly as possible over a relatively long period of time. In this connection it should be noted that proteins in comparison to low molecular substances have specific characteristics due to their complex structure, their high molecular weight and the low degree of loading that is necessary due to their high biological efficacy which make it difficult to microencapsulate them successfully. Hence depending on the type of microencapsulation method used the protein stability can be adversely affected and the release may not be optimal or there may be an unsatisfactory release profile. The release behaviour is influenced on the one hand by the high molecular weight and the hydrophilic structure but also on the other hand by stability problems (including aggregation) of the protein and the low degree of loading.

One of the most important production methods for microparticles such as for example microcapsules or microbeads is the so-called triple emulsion process which has already been used for the microencapsulation of proteins. Basically in this method, which is also referred to as the W/O/W technique, the active substance is dissolved or suspended in an aqueous solution and this aqueous solution is homogenized with an oily solution of an organic water-immiscible solvent containing a polymer to form a W/O emulsion. This W/O emulsion is dispersed in a solution containing an aqueous stabilizer (external aqueous phase) so that an emulsion with three phases (triple emulsion) is formed. The solvent is then evaporated by various techniques which results in a hardening of the microparticles. The hardened microparticles are collected by centrifugation and/or filtration and, after washing with water or suitable aqueous solvents, dried by lyophilization or vacuum drying at room temperature. The polymers that are usually used are polymers of lactic acid (LA=lactic acid) and glycolic acid (GA=glycolic acid) or copolymers thereof (PLGA) with molecular weights between 2,000 and 100,000 and a ratio of lactic acid to glycolic acid between 100:0 to 50:50.

The residual content of solvent in the microparticles may prove to be problematic when using the triple emulsion method (R. Jalil and J. R. Nixon, J. Microencapsulation 7 (3), 1990, p. 297–325) since the dichloromethane which is used most frequently as the polymer solvent appears to be critical from a toxicological point of view. The residual content of solvent should also be kept as small as possible due to its potential influence on the polymer properties and the stability of the active substance in the polymer matrix.

The production of microcapsules with the aid of the triple emulsion method is disclosed for example in the European Patent Application EP 0 145 240 (Takeda) wherein the inner aqueous phase has a viscosity of at least 5,000 mPas or is completely solidified. The viscosity is increased by auxiliary substances such as gelatin, human serum albumin, globulin, casein, collagen and polyamino acids. The microencapsulation of γ interferon and heparin is described in application examples.

The same production process is described in the Patent document EP 0 190 833 (Takeda) except that in this case the viscosity of the W/O emulsion is set at a value between 150–10,000 mPas. This is achieved by varying the polymer concentration (PLGA 100/0–50/50) and by adding natural or synthetic high molecular compounds such as e.g. proteins, carbohydrates (cellulose, dextrin, pectin, starch, agar), polyvinyl compounds, polycarboxylic acids or polyethylene compounds to the aqueous phase. This is intended to greatly reduce the tendency of the microparticles to aggregate and cohere during their production. In one application example interferon alpha is encapsulated.

In EP 0 442 671 (Takeda) similar statements to those in EP 0 190 833 are made with regard to aggregation properties, spherical shape of the microparticles and potential additives. According to the patent document "substances retaining the medicinal substance" are not absolutely necessary. The examples that are specifically disclosed and elucidated in more detail in the description relate to the short chained and relatively stable peptide TAP144 which is an LHRH analogue.

Examples of the microencapsulation of peptides and proteins with the aid of the W/O/W technique are also published in the technical literature.

Thus Ogawa et al., (Chem. Pharm. Bull. 1988, vol. 36, No. 3, p. 1095–1103) describe the microencapsulation of leuprorelin acetate, a peptide, using PLA (polymer of lactic acid) and PLGA and also elaborate on the release behaviour of the peptide.

Cohen et al., (Pharmaceutical Research 1991, vol. 8, No. 6, p. 713) encapsulated FITC horseradish peroxidase and FITC-BSA in PLGA microparticles with a molecular weight of 14,000 or less and a ratio of lactic acid/glycolic acid of 75/25 and found that the protein BSA was undamaged and that the enzyme activity was preserved. Jeffery H et al. (Pharmaceutical Research 1993, vol. 10, No. 3, p. 362) used ovalbumin as the core material and were able to demonstrate the intactness of the released protein. M. S. Hora et al., (Biotechnology 1990, vol. 8, p. 755) used interleukin 2 and modified forms thereof as the core material and examined the release behaviour of PLGA microparticles which contained human serum albumin as an excipient.

In addition various processes for the production of microparticles based on PLA or PLGA polymers and the influence of additives on the protein stability were examined in more detail in various publications based on model substances for proteins (cf. W. Lu and G. Park, PDA Journal of Pharmaceutical Science & Technology, 1995, 49: 13–19; M.-K. Yeh et al., Journal of Controlled Release, 1995, 33: 437–445; M. J. Alonso et al., Vaccine, 1995, 12: 299–306; J. P. McGee et al., Journal of Controlled Release, 1995, 34: 77–86). Ovalbumin, tetanus toxoid and carboanhydrase were used in these cases as model proteins.

Youxin L. et al. (Journal of Controlled Release 32, (1994) 121–128) describe depot forms of ABA triblock copolymers (MW: 15,000–40,000) the A block of which is a copolymer of lactic acid and glycolic acid and the B block of which is a polyethylene glycol chain (PEG). They found that these microparticles rapidly and continuously released bovine serum albumin over 2–3 weeks which is relatively insensitive to aggregation and was used as a model protein at a high degree of loading (ca. 3–4% w/w) (polymer composition LA:GA:PEG=48:14:38 [mol %]).

The PLGA polymers that have up to now often been used to produce microcapsules have the major disadvantage of a low swelling capability due to their hydrophobic properties as a result of which water can only slowly enter into the interior of the depot form. This impedes the diffusion of the protein molecules through the polymer layers which results in an unsatisfactory release rate. This is especially the case when very small amounts of polypeptide are included in the microparticles i.e. at a low degree of loading. Furthermore the slow uptake of water results in a high local protein concentration due to the small amount of water that is available which promotes the formation of high molecular protein aggregates. These in turn can no longer be released due to their high molecular weight. A therapeutically reliable dosing of the active substance can then no longer be guaranteed. Furthermore the high proportion of protein aggregates can result in undesired immunological reactions. Only very stable proteins with relatively high degrees of loading of for example more than 5% can be released at an acceptable rate and without forming aggregates over a relatively long period of time.

Moreover hydrophilic ABA triblock copolymers cannot even ensure a continuous release of polypeptides over a time period of two weeks when the content of polypeptide in the microparticles is very low (i.e. when the degree of loading is low). A low degree of loading is present when only small amounts of polypeptides are embedded in the polymer. A similar disadvantageous release behaviour is found when polypeptides that are susceptible to aggregation are used. In these cases an increased formation of aggregates and unacceptable release periods of less than 2 weeks are also observed with the hydrophilic ABA triblock copolymer. This leads overall to unsatisfactory release rates of the active substance from the polymer.

The object of the invention was to produce polypeptide-containing microparticles in which it is intended to keep the aggregation of the active substance as low as possible or to substantially avoid it even for polypeptides that are susceptible to aggregation so that the polypeptide that is contained in the microparticles is as intact as possible. The microparticles should ensure a continuous release of the polypeptides over a time period of at least two weeks. This should above all be achieved with microparticles which have a low degree of loading of the active substance. In particular these release periods should apply to low amounts of polypeptide of up to about 3% (relative to the total amount of microparticle).

In addition the object of the invention was to provide a microencapsulation process which can be used to produce these desired microparticles and which ensures a toxicologically acceptable residual content of solvent in the microparticles.

The object of the invention is achieved by microparticles which are composed of a biodegradable polymer matrix in which the polypeptide is embedded wherein an ABA triblock copolymer is used as the polymer, the A block of which is a copolymer of lactic acid and glycolic acid and the B block of which is a polyethylene glycol chain, and which contain additives that are selected from the group comprising serum proteins, polyamino acids, cyclodextrins; cyclodextrin derivatives; saccharides such as e.g. disaccharides and polysaccharides; amino sugars; amino acids; detergents; organic carboxylic acids as well as mixtures of these additives.

The disaccharides trehalose, sucrose and maltose come for example into consideration as saccharides. Polysaccharides are for example raffinose, starch, maltodextrin, alginates or dextran. A suitable amino sugar is for example chitosan. A preferred cyclodextrin derivative within the sense of the invention is for example beta hydroxypropyl cyclo-dextrin (HPCD). Human serum albumin and bovine serum albumin come into special consideration as serum proteins.

Aliphatic and cyclic monocarboxylic acids are suitable as organic carboxylic acids such as benzoic acid, acetic acid, propionic acid, butyric acid, isobutyric acid, valeric acid, acrylic acid, crotonic acid as well as derivatives thereof substituted by hydroxy groups such as e.g. p-hydroxybenzoic acid, β-hydroxybutyric acid, salicylic acid, lactic acid or glycolic acid. Benzoic acid is especially suitable. In the production of the microparticles the carboxylic acids are essentially added to the organic phase (polymer phase) in which the polymer is dissolved or suspended. The added amount of carboxylic acids is in the range of up to 30% by weight relative to the amount of the final microparticles preferably up to 20% by weight and in particular 1–15% by weight. The use of monocarboxylic acids such as e.g. benzoic acid as an additive surprisingly leads to an improvement of the release of the polypeptides from the microparticles. In this connection the addition of carboxylic acids was not found to result in the expected accelerated degradation of polymer in the case of the ABA triblock copolymers.

Mixtures of the above-mentioned additives are also advantageous within the sense of the invention. Examples are mixtures of dextrans and polyamino acids. Thus for example mixtures of dextran and poly-L-arginine or dextran and poly-L-histidine are particularly advantageous with respect to lowering the aggregate formation of the polypeptide in the microparticle. Mixtures of cyclodextrins or cyclodextrin derivatives with amino acids or polyamino acids are also preferred as additives. Detergents and triglycerides such as for example Tween 20®, Tween 80®, Pluronic® or Miglyol® are also suitable within the sense of the invention as additives.

The corresponding (D) or (L) or poly-(D,L) amino acids come into consideration as polyamino acids. Polyarginine is particularly preferred with a molecular weight of 5,000–150,000, in particular 5,000 to 50,000 as well as polyhistidine with a molecular weight of 5,000–50,000 in particular 15,000–50,000.

Using the said additives according to the invention it is possible to reduce the total amount of aggregate in the polypeptide to below 5%.

Polypeptides which come into consideration within the sense of the invention are physiologically active polypeptides with a molecular weight between 2,000 and 200,000 D. The molecular weight is preferably at least 5,000, 10,000 or 20,000 D. In particular polypeptides with a molecular weight of up to 100,000 preferably up to 50,000 Daltons come into consideration. Such polypeptides are in particular biologically active macromolecules, muteins thereof, analogues, as well as deletion or substitution variants which can be used for therapeutic purposes. The following polypeptides are mentioned as examples: erythropoietin (EPO), parathormone (PTH), G-CSF, TNF, NGF or EGF as well as derivatives thereof that can be derived by deletions or substitutions in the amino acid chain. Further polypeptides are: interferons (α, β, γ interferon), colony-stimulating factors, interleukins, macrophage-activating factors, B-cell factors, T-cell factors, immunotoxins, lymphotoxins, TGF, thrombopoietin (TPO), renin inhibitors, collagenase inhibitors, EGF, growth hormones, PDGF, bone growth factors, BMP (bone morphogenic proteins), insulin, IGF-BP (insulin-like growth factor binding proteins), ANP (atrial natriuretic peptides), calcitonin, FSH, LH, NGF, glucagon, TSH (thyroid stimulating hormone), monoclonal or polyclonal antibodies. Particularly preferred polypeptides within the sense of the present invention are polypeptides that are susceptible to aggregation such as for example EPO.

The polypeptide content in the microparticles is between 0.01 to 5% by weight relative to the total amount of microparticle. The degree of loading is preferably 0.1–3% by weight, in particular 0.1–2% by weight and preferably 0.1–1% by weight. In particular the microparticles can be produced with a very low degree of loading of up to 1% by weight. In the case of proteins that are susceptible to aggregation the preferred degree of loading is 0.1–1% in particular 0.2–0.6%. A degree of loading of about 0.01; 0.05 or 0.1% by weight comes into consideration as the lower limit. The amount of the active substance contained in the microparticles depends on the dosage which has to be determined in each individual case and the therapeutic range of the respective active substance. In the case of EPO the amount of active substance is about 10 μg–100 μg per 10 mg microparticle amount. In particular about 10–70 μg, preferably 30–50 μg are used. With a specific EPO activity of about 160,000 U/mg this corresponds to a dosage of 1,600–16,000 U per 10 mg microparticle amount (10–100 μg per 10 mg microparticle amount). The amount of microparticles that has to be administered is preferably determined on the basis of the desired dosage of EPO (in U). If for example the degree of loading is 0.4% (corresponds to 40 μg EPO per 10 mg microparticle) and the dosage of EPO should be 20,000 U (corresponds to 125 μg EPO), the amount of microparticles that has to be administered is 31.25 mg. This amount corresponds to an estimated monthly dose of EPO in the DDS system.

Surprisingly it was found that the use of ABA triblock copolymers in combination with additives enables a continuous release of the polypeptides over a relatively long period of time—but of at least two weeks—and that the additives considerably reduce the aggregation. According to the invention ABA block polymers come into consideration, the A block of which has a molecular weight between 2,000 and 150,000 and the B block of which has a molecular weight between 1,000 and 15,000. In particular the B block has a molecular weight of between 3,000 to 10,000. ABA block polymers are particularly preferred with a molecular weight of 5,000–50,000 Daltons preferably 10,000–30,000 and a polydispersity of 1.1–8.5 or 1.1–5.5 preferably 1.5–4.5 and especially preferably of 2–4.

Table 5 gives an overview of the ABA copolymers used according to the invention whose composition differs with regard to the ratio of lactide/glycolide/PEG, the molecular weight and polydispersity. According to the invention the amount of polyethylene glycol (PEG proportion) in the block polymer is 20 to 50 mol % relative to the total amount of polymer and preferably 25 to 45 mol %. A PEG proportion of 30 to 40 mol % in particular 30 to 38 mol % and preferably 30 to 35 mol % has proven to be particularly advantageous for the duration of release and for the continued release of the active substance. The percentage of PEG in the ABA block copolymer is preferably about 32 to 33 mol %.

The percentage of LA in the ABA block copolymer is preferably 40 to 60 mol % in particular 45–60 mol %. Mole percentages of about 46%, 51% or 57% are preferred. The percentage of GA in the ABA block copolymer is preferably 5 to 25% in particular 10 to 25%. Preferred percentages are about 11%, 16% or 22%.

The ratio of lactic acid to glycolic acid in the block polymer is between 1:1 and 5:1 in particular it is between 1.5:1 and 4.5:1. A ratio of LA/GA of about 2:1 to 4:1 is particularly preferred. Particularly preferred ABA triblock copolymers according to the invention are polymers with a ratio of LA/GA=4:1 and a content of polyethylene glycol of 30–38%. In particular a polymer with a ratio of LA:GA:PEG=57:11:32; 51:16:33; 50:12:38 or 46:22:32 comes into consideration.

The latter polymer modifications offer an optimum with regard to degradation rate and PEG content. A higher PEG content does indeed lead to a more rapid degradation but on the other hand it also leads to an impairment of the mechanical properties of the microparticles and possibly also to interactions between PEG and the polypeptide.

The ABA triblock copolymers can be produced according to processes known in the literature (see Journal of Controlled Release 27, 1993, 247–257).

Surprisingly it was found that, in addition to their aggregation-reducing effect, the additives according to the invention can result in a significant increase of the release period compared to ABA microparticles without additives. This applies in particular to the serum proteins according to the invention which cause an increase of the release period of the polypeptide of for example up to 29 days (of example 4). Bovine or human serum albumin are preferably used as serum proteins. If the additives according to the invention and in particular BSA and beta hydroxypropyl cyclodextrin are added to PLGA microparticles then an aggregation-reducing effect also occurs and thus a stabilization of the polypeptides that are susceptible to aggregation.

Such long release periods of up to 29 days for polypeptides from microparticles based on PLGA or ABA triblock copolymers have only previously been known in those cases where there has been a high degree of loading but not for cases in which the amount of active substance in the microparticles is very low such as for example in the case of EPO. If EPO is embedded in the ABA microparticles at a higher degree of loading (e.g. ca. 3%), the protein is released over 29 days (cf. tab. 4B). In particular it was found that an extended release is achieved when a monocarboxylic acid, in particular benzoic acid is added to the polymer phase during the production of the microparticles. This applies especially to the case of the aforementioned low degrees of loading.

The microparticles according to the invention can also contain amino acids such as arginine, glycine, lysine or phenylalanine, cyclodextrins or cyclodextrin derivatives such as e.g. beta hydroxypropyl cyclodextrin (HPCD) as additives. Polyamino acids such as e.g. polyarginine or polyhistidine can also be used as additives according to the invention or even mixtures of cyclodextrin or cyclodextrin derivatives with amino acids or polyamino acids such as e.g. HPCD with polyarginine. Mixtures of dextrans with cyclodextrin derivatives such as HPCD or with cyclodextrins can also be used. The dextrans used have a molecular weight between 20,000 and 60,000, dextran 40,000 being particularly preferred.

Mixtures of dextrans and polyarginine or mixtures composed of dextrans and polyhistidine are particularly preferably used as additives according to the invention in addition to serum proteins.

The microparticles according to the invention contain additives in an amount of 0.5–40% by weight in relation to the total amount of microparticles, preferably of 1–30%.

1–20% by weight is especially preferable. In the case of saccharides amounts of 5–15% by weight are preferably used. In the case of polyamino acids the amount of additives is preferably 1–5% by weight. cyclodextrin and cyclodextrin derivatives are preferably added in an amount of 2–20% by weight. The amount of BSA or HSA is preferably 2–20% by weight relative to the total particle weight. The amount of carboxylic acids is in particular up to 15% preferably about 10%.

The invention also concerns a process for the production of microparticles containing polypeptide with the aid of the triple emulsion process which is characterized in that in the production of the oily or organic phase by dissolving a polymer in an organic water-immiscible solvent, an ABA triblock copolymer is used as a polymer the A block of which is a copolymer of lactic acid and glycolic acid and the B block of which is a polyethylene glycol chain, and additives that are selected from the group comprising serum proteins, polyamino acids, cyclodextrins, cyclodextrin derivatives, saccharides such as disaccharides and polysaccharides, amino sugars, amino acids, detergents or carboxylic acids as well as mixtures thereof are added to the aqueously dissolved polypeptide which is emulsified in the organic phase.

It has turned out that the first homogenization step (formation of the W/O emulsion) appears to be responsible for the formation of polypeptide aggregates. Thus according to the invention the dispersing period is shortened from 60 to 30 seconds, an Ultra Turrax is used as a homogenizer and the weight ratio of water/organic phase (preferably dichloromethane) is increased from 5 to up to 20% (percentage by weight). Preferably it is dispersed twice for about 30 seconds with an interval of 30 seconds in the first homogenization step. It is particularly preferable to disperse once for about 30 seconds. This modification of the production conditions results in the amount of aggregate to be decreased slightly.

Within the sense of the production process according to the invention it is particularly advantageous to cool all solutions and equipment to 0–16° C. during the entire production period of the production process. This achieves a particularly favourable reduction of aggregate. In this case it is even possible to largely omit the addition of aggregation-inhibiting additives. In comparison to the production of microparticles at room temperature it was possible in this manner to achieve a significant reduction of the content of aggregate in the polypeptides used in the microparticles (reduction of 10–20% content of aggregate to a content of aggregate of 2–5%).

The weight ratio water/organic phase of 20–25% (3–4 parts organic solvent/one part of water) additionally enable a larger amount of additives to be introduced into the inner aqueous phase.

The microparticles according to the invention also surprisingly have an extremely low residual content of solvent. The microparticles produced with the ABA polymer contain less than 1% preferably less than 0.1% in particular less than 0.01% residual solvent such as e.g. dichloromethane. Apparently the selected process parameters achieve an almost complete removal of the dichloromethane from the microparticles that are formed which is above all due to the favourable volume ratio of the organic to the external aqueous phase.

In order to exclude the influence of residual water on the protein stability, the residual water content in the microparticles was also determined. The determined water content of 0.2% showed that it was possible to almost completely remove the amount of water in the inner aqueous phase that was used.

Investigations on the storage stability of the microparticles according to the invention have shown that these are stable on storage for at least two months at room temperature (20–25° C.) and that no changes occur with regard to aggregate formation and release properties.

A further subject matter of the invention is the use of pharmaceutical additives selected from the group comprising serum proteins, polyamino acids, cyclodextrins, cyclodextrin derivatives, saccharides, amino sugars, amino acids, detergents as well as mixtures of these additives to avoid aggregate formation of polypeptides susceptible to aggregation in the production of polypeptide-containing microparticles.

The invention is elucidated further in the following application examples without limiting it thereto.

EXAMPLE 1

Process for the Production of Microparticles Containing EPO (W/O/W Process)

A D,L-PLGA polymer (LA:GA=50:50; RG503) was obtained from Boehringer Ingelheim and an ABA copolymer (LA:GA:PEG=50:12:38) was produced as described in the Journal of Controlled Release 27, 1993, 247–257.

One solution each of the D,L-PLGA and ABA block polymer in dichloromethane was produced in which 700 mg of the polymer was dissolved in 2.5 ml (3.3 g) dichloromethane. 3.5 mg EPO (in 0.2 ml sodium phosphate buffer, pH 7.4) is admixed as required with additives (1% –20% by weight relative to the total amount of microparticles) and filled up with water to a final volume of 0.8 ml (0.8 g).

The aqueous EPO solution is added to the polymer solution and a W/O emulsion is prepared with the aid of an Ultra Turrax (30 seconds, 30 seconds interval, again 30 seconds, 20–24° C., 20,000 rpm and again for 30 seconds). Subsequently the W/O emulsion is dispersed by injection into 300 ml aqueous 0.1% PVA solution with the aid of an Ultra Turrax at 8000 rpm for 30 seconds (production of a W/O/W triple emulsion).

The W/O/W emulsion is stirred for 2 to 3 hours at room temperature with the aid of a paddle mixer to evaporate the organic dichloromethane phase (solvent evaporation). The hardened MP that form are isolated by suction filtration, washed twice with 200 ml water each time and lyophilized. The microparticles are stored over blue gel at 4° C.–8° C. in a desiccator.

EXAMPLE 2

Stabilization of Microparticles Containing EPO

Microparticles were prepared by conventional methods as described in example 1 and various additives in various amounts relative to the total amount of microparticles were added.

The aggregate formation of the active substance EPO was subsequently determined as follows by means of SDS-PAGE after extracting EPO from the microparticles (a) or solvating the microparticles in DMSO or a DMSO/DMF mixture (30:70) (b):

a) 10 mg MP was dissolved in 300 $\mu$l $CH_2Cl_2$ and EPO was precipitated by adding 700 $\mu$l acetone. The EPO precipitate was centrifuged, washed twice with 1 ml $CH_2Cl_2$/acetone mixture (1:3) and subsequently dried in a speed vac. The precipitate was dissolved in sample buffer for SDS-PAGE (composition: 60 mM Tris-HCl, pH 6.8; 2% SDS; 10% glycerol; 0.001% bromophenol blue), applied to a 12.5 or 15% SDS gel and subjected to electrophoresis.

b) 10 mg MP was dissolved in 200 $\mu$l DMSO/DMF (30:70). 25 $\mu$l (corresponds to ca. 5 $\mu$g EPO) was loaded directly onto a 15% SDS gel and subjected to electrophoresis.

After the electrophoresis was completed the gels were either:

aa) stained with Coomassie and measured densitometrically by means of a laser scanner or bb) blotted on nitrocellulose, the EPO-containing bands stained with an EPO-specific antibody and measured densitometrically by means of a laser scanner.

It turned out that in ABA microparticles (LA:GA:PEG= 50:12:38) the total amount of EPO aggregate of ca. 15–30% could be reduced to below 1% by embedding BSA. Furthermore poly-L-arginine and poly-L-histidine also in combination with dextran 40,000 had a significant aggregate-reducing effect. These additives were used in an amount of 1 to 10% by weight relative to the total amount of microparticle (cf. table 1).

The additives also resulted in a reduction of an aggregate in EPO-PLGA microparticles. In this case BSA and β-hydroxypropyl cyclodextrin in particular proved to be extremely effective (amount of aggregate below 1%) (cf. table 2). In contrast in the microparticles containing PEG as the additive an increase of the amount of aggregate was found. Furthermore in the case of microparticles containing PEG or Pluronic F127 with a content of auxiliary substances of at least 4% an increased occurrence of deformed microparticles was observed.

TABLE 1

Additives and their influence on the aggregate situation

| Additive | % ww of the total particle | aggregation<br>↑ = increased<br>— = unchanged<br>↓ = lowered |
|---|---|---|
| without (room temperture) | | 10–20% |
| without (0–4° C.) | | ↓ |
| bovine serum albumin | 5 | ↓↓↓ |
| bovine serum albumin | 10 | ↓↓↓ |
| dextran 40,000 | 5 | ↓ |
| dextran 20,000 | 5 | — |
| poly-L-arginine | 1–5 | ↓↓ |
| poly-L-histidine | 1–5 | ↓↓ |
| poly-L-arginine | 2.5 | ↓ |
| β-hydroxypropyl cyclodextrin | 2.5 | |
| dextran 40,000 | 2.5 | ↓↓ |
| β-hydroxypropyl cyclodextrin | 2.5 | |
| poly-L-arginine | 1–5 | ↓↓ |
| dextran 40,000 | 5 | |
| poly-L-histidine | 1–5 | ↓↓ |
| dextran 40,000 | 5 | |
| β-hydroxypropyl cyclodextrin | 5–15 | ↓ |
| arginine | 5 | ↓ |
| benzoic acid | 10 | — |
| Tween 20 | 0.5 | ↓ |
| Pluronic F68 | 0.5 | ↓ |
| Pluronic F127 | 0.5 | ↓ |
| reference: | Δ | ↑↑ |
| 100 mM sodium phosphate | 15 | |

TABLE 2

Additives and their influence on the aggregate situation in PLGA microparticles

| Additive | % ww of the total particle | aggregation<br>↑ = increased<br>— = unchanged<br>↓ = lowered | initial burst [%] |
|---|---|---|---|
| without | | 8–10% | 29 |
| BSA | 5 | ↓↓ | 40 |
| BSA | 10 | ↓↓ | 40 |
| CD | 5 | ↓↓ | 30 |
| CD | 10 | ↓↓ | 40 |
| CD | 15 | ↓↓ | 40 |
| CD/PEG 10,000 | 5/5 | ↓ | 7 |
| CD/Pluronic F127 | 5/5 | ↓ | 8 |
| CD/trehalose | 5/5 | ↓ | 30 |
| dextran 40,000 | 5 | ↓ | 10 |
| D40/poly-(L)-arginine | 5/1 | ↓ | n.d. |
| arginine | 0.2 | ↓ | 15 |
| arginine | 4.8 | ↓ | 18 |
| PEG 1,550 | 0.43 | — | 12 |
| PEG 1,550 | 4.3 | ↑ | 1.3 |
| PEG 10,000 | 10 | ↑ | 0.6 |
| PEG 35,000 | 10 | ↑ | n.d. |
| Pluronic F127 | 10 | ↑ | 20 | n.d.: not determined

EXAMPLE 3

Influence of Additives on the Release of EPO from PLGA Microparticles

Microparticles based on D,L-PLGA polymers (RG503, MW=40,000; LA:GA=50:50; polydispersity 2.4) with a content of the active substance EPO of 0.5% (relative to the total amount of microparticles) were prepared according to example 1 and various additives (% w/w relative to the total amount of microparticles) were added during the preparation.

The determination of the release rate (in % of the encapsulated amount of active substance/per day) was carried out as follows:

In each case 15 mg microparticles was weighed into 2 ml Eppendorf vessels and admixed with 1.5 ml PBS buffer and 0.01% Tween 20, pH 7.4. These tubes were placed in a rotating metal block (Rotatherm Liebisch Co. 30 rpm) thermostated at 37° C. Samples were taken at the predetermined sampling times and the remaining release medium was each time completely replaced by new medium. The release rates of the following microparticles were determined.

TABLE 3

In vitro release of EPO from PLGA (50:50) microparticles.
Release in %/day (relative to the total amount EPO present in the MP)

| | day: | | | | | | | | | |
|---|---|---|---|---|---|---|---|---|---|---|
| additive | 1 | 2 | 3 | 7 | 11 | 14 | 18 | 21 | 25 | 29 |
| without | 29 | — | — | — | — | — | — | — | — | — |
| 10% BSA | 40 | — | — | — | — | — | — | — | — | — |
| 10% HPCD | 36 | — | — | — | — | — | — | — | — | — |
| 5% Arg | 19 | 0.1 | 0.05 | — | — | — | — | — | — | — |
| 5% dextr 40 | 9.2 | 0.2 | — | — | — | — | — | — | — | — |
| 5% dextr 40<br>1% polyarg | 5.7 | 0.3 | — | — | — | — | — | — | — | — | dextr 40: dextran 40,000
polyarg: polyarginine
Arg: arginine
HPCD: β-hydroxypropyl cyclodextrin
BSA: bovine serum albumin It is clear from these results that in PLGA microparticles the EPO release only lasts for a maximum of 24–36 hours independent of the additives and then there is no further continuous release. The additives only change the level of the initial burst. A protracted release of EPO could not be achieved with the additives.

EXAMPLE 4
Influence of Additives on the Release of EPO from ABA Microparticles Microparticles based on ABA triblock copolymer with LA:GA:PEG=57:11:32 (polymer A) and LA:GA:PEG=50:12:38 (polymer B) with a content of the active substance EPO of 0.5% by weight each time (relative to the total amount of microparticles) were prepared according to example 1 and various additives (% w/w relative to the total amount of microparticles) were added. The determination of the release rates was carried out as described in example 3. The results are summarized in table 4A. The polymers A and B were qualitatively as far as possible comparable with regard to their release properties of the active substance.

TABLE 4A

In vitro release of EPO from ABA microparticles (at a degree of loading of 5%).
Release in %/day (relative to the total amount of EPO present in the microparticles)

| additive | day: | | | | | | | | | |
|---|---|---|---|---|---|---|---|---|---|---|
| | 1 | 2 | 3 | 7 | 11 | 14 | 18 | 21 | 25 | 29 |
| without | 12.7 | 1.8 | 0.5 | 0.26 | 0.02 | — | — | — | — | — |
| 5% BSA | 4.6 | 1.6 | 0.5 | 0.4 | 0.12 | 0.06 | 0.07 | 0.04 | 0.03 | 0.04 |
| 10% BSA | 3.7 | 1.6 | 0.4 | 0.4 | 0.25 | 0.14 | 0.11 | 0.08 | 0.04 | 0.04 |
| 5% dextr 40 | 9.0 | 1.1 | n.d. | 0.85 | 0.3 | 0.22 | 0.1 | — | — | — |
| 5% dextr 40 1% polyarg | 17.0 | 3.0 | n.d. | 2.8 | 1.3 | 0.34 | 0.17 | — | | |
| 10% benzoic acid* | 18.4 | 3.9 | 3.4 | 2.5 | 1.3 | 0.7 | 0.2 | 0.1 | — | — |
| 10% HPCD | 23.2 | 3.1 | 2.0 | 1.2 | 0.5 | 0.12 | 0.07 | — | — | — |
| 5% Arg | 38 | 4.5 | 3.5 | 0.7 | 0.3 | 0.03 | 0.02 | — | — | — | dextr 40: dextran 40,000
polyarg: polyarginine
Arg: arginine
HPCD: β-hydroxypropyl cyclodextrin
BSA: bovine seruin albumin
n.d. not determined
*additive added to the polymer phase It can be seen from table 4 A that it is possible to achieve a continuous release of EPO up to for example the 29th day when using ABA microparticles compared to PLGA microparticles in particular when BSA is used as the additive.

If the in vitro release of EPO from PLGA (50:50) microparticles and ABA microparticles with various monomer compositions having a content of active substance of 0.5% and 3.4%—without additives in each case—is compared then it becomes clear that the ABA microparticles according to the invention are superior.

It can be seen from table 4 B that the release from ABA microparticles is limited to 11–18 days at a low degree of loading (0.5%) when no additives are added. In the case of ABA triblock copolymers an increased period of release can be observed compared to PLGA microparticles the same degree of loading. The release period increases with a higher content of GA in the ABA triblock copolymers (see above, longer release with asing content of GA of 11, 16 or 22% by weight).

EXAMPLE 5

The chemical and physical properties of some ABA block polymers are summarized in the following table 5.

TABLE 5

List of ABA triblock copolymers used

| Batch | LA/GA/PEG % | MW [Da] | Tg [° C.] | polydispersity |
|---|---|---|---|---|
| 1 | 64/13/23 | 25,000 | 47.9 | 3.1 |
| 2 | 57/11/32 | 19,000 | 46.3 | 2.5 |

TABLE 4B

Comparison of the in vitro release of EPO from PLGA and ABA microparticles with various monomer compositions and different degrees of loading, without further additives. Release in %/day (relative to the total amount of EPO present in the microparticles)

| MP made of polymer degree of loading (in %) | | day: | | | | | | | | | |
|---|---|---|---|---|---|---|---|---|---|---|---|
| | | 1 | 2 | 3 | 7 | 11 | 14 | 18 | 21 | 25 | 29 |
| PLGA (50:50) | (0.5%) | 29 | — | — | — | — | — | — | — | — | — |
| ABA (57:11:32) | (0.5%) | 12.7 | 1.8 | 0.5 | 0.26 | 0.02 | — | — | — | — | — |
| ABA (51:16:33) | (0.5%) | 31 | n.d. | 1.6 | 0.7 | 0.4 | 0.1 | — | — | — | — |
| ABA (46:22:32) | (0.5%) | 15 | n.d. | 3.2 | 1.0 | 0.5 | 0.2 | 0.1 | — | — | — |
| ABA (51:16:33) | (3.4%) | 11.7 | 2.2 | 1.8 | 0.8 | 0.2 | 0.17 | 0.2 | 0.2 | 0.13 | 0.1 | n.d. = not determined

TABLE 5-continued

List of ABA triblock copolymers used

| Batch | LA/GA/PEG % | MW [Da] | Tg [° C.] | polydispersity |
|---|---|---|---|---|
| 3 | 50/12/38 | 20,000 | 46.1 | 2.3 |
| 4 | 45/9/46 | 17,000 | 42.1 | 2.8 |
| 5 | 36/35/29 | 16,400 | 35.3 | 6.8 |
| 6 | 46/22/32 | 16,700 | 45.1 | 5.4 |
| 7 | 42/28/30 | 17,200 | 31.1 | 8.4 |
| 8 | 51/16/33 | 18,500 | 47.9 | 4.6 |
| 9 | 40/20/40 | 13,500 | 23.7 | 5.2 |

The microparticles containing EPO prepared from the ABA triblock copolymers listed in table 5 had glass transition temperatures (Tg) in the range of 27–45° C. Thus it is possible to stably store the microparticles for long time periods in a refrigerator (4–8° C.).

EXAMPLE 6

Production of microparticles while cooling in order to reduce aggregate formation.

The microparticles were produced as described in example 1 with the following modifications:

All solutions (dichloromethane polymer solution, EPO solution in sodium phosphate buffer and PVA solution) were precooled in an ice-bath (0° C.) in a cold room. All vessels and apparatuses (e.g. Ultra Turrax) were pre-cooled in a cold room (4° C). All steps for producing the microparticles, including stirring the W/O/W emulsion, hardening the microparticles and evaporating the dichloromethane, were carried out in an ice-bath in a cold room. The temperature measured in the 0.1% PVA solution after production of the W/O/W emulsion was 1° C.

The microparticles produced in this way had the following advantages properties: the practical degree of loading of EPO was larger than for standard process (0.54% instead of 0.4%). The aggregate content in the microparticles without stabilizing additives was less (2–5% instead of 10–20%). The aggregate content was in this case determined analogously to the method described in example 2.

List of Abbreviations
MP: microparticles
PLGA: copolymer composed of lactic acid and glycolic acid
LA: lactic acid
GA: glycolic acid
ABA: triple block copolymer composed of A block and B block
A block: copolymer of lactic and glycolic acid
B block: polyethylene glycol (peg)
BSA: bovine serum albumin
HSA: human serum albumin
PVA: polyvinylalcohol
D40 dextran 40,000

What is claimed is:

1. A pharmaceutical composition, comprising microparticles of a biodegradable polymer matrix in which an active substance having a nonzero degree of loading of up to about 3% is embedded, wherein the polymer is an ABA triblock copolymer, wherein A represents a copolymer of lactic acid and glycolic acid and B represents a polyethylene glycol chain, the active substance is a physiologically active polypeptide, and wherein the microparticle contains an additive comprising at least one member selected from the group consisting of (1) a disaccharide, (2) dextran having a molecular weight of 20,000 to 60,000 Daltons, (3) an amino sugar, (4) an amino acid, (5) a detergent, (6) a mixture of dextran having a molecular weight of 20,000 to 60,000 Daltons and a cyclodextrin or derivative thereof, (7) a mixture of dextran having a molecular weight of 20,000 to 60,000 Daltons and a polyamino acid, and (8) a mixture of dextran having a molecular weight of 20,000 to 60,000 Daltons and an amino acid, wherein the additive is contained in the pharmaceutical composition in an amount of 1 to 20% by weight in relation to the total weight of the microparticles and the additive substantially prevents aggregation of the physiologically active polypeptide and provides a lower rate of release of the physiologically active polypeptide from the microparticle than a corresponding pharmaceutical composition without the additive.

2. The pharmaceutical composition of claim 1, wherein the additive comprises at least one member selected from the group consisting of an amino acid, a disaccharide, dextran having a molecular weight of 20,000 to 60,000 Daltons and a detergent.

3. The pharmaceutical composition of claim 1, wherein the additive comprises a mixture selected from the group consisting of (1) dextran having a molecular weight of 20,000 to 60,000 Daltons and a polyamino acid, (2) a cyclodextrin or derivative thereof and dextran having a molecular weight of 20,000 to 60,000 Daltons, and (3) dextran having a molecular weight of 20,000 to 60,000 Daltons and an amino acid.

4. The pharmaceutical composition of claim 1, wherein the polyamino acid is selected from the group consisting of polyarginine having a molecular weight of 5,000 to 150,000 Daltons and polyhistidine having a molecular weight of 5,000 to 50,000 Daltons.

5. The pharmaceutical composition of claim 1, wherein the physiologically active polypeptide has a molecular weight of 2,000 to 200,000 Daltons.

6. The pharmaceutical composition of claim 5, wherein the polypeptide is selected from the group consisting of EPO, PTH, TNF, NGF, EGF, α-interferon, β-interferon, γ-interferon, a colony-stimulating factor, an interleukin, a macrophage-activating factor, a B-cell factor, a T-cell factor, an immunotoxin, a lymphotoxin, TGF, TPO, a renin inhibitor, a collagenase inhibitor, EGF, a growth hormone, PDGF, a bone growth factor, a bone morphogenic protein, insulin, an insulin-like growth factor binding protein, an atrial natriuretic peptide, calcitonin, FSH, LH, NGF, glucagon, TSH, and a monoclonal or polyclonal antibody.

7. The pharmaceutical composition of claim 1, wherein the physiologically active polypeptide is present in an amount of from 0.01 to 5% by weight.

8. Tjee pharmaceutical composition of claim 1, wherein the physiologically active polypeptide is aggregation-susceptible.

9. The pharmaceutical composition of claim 8, wherein the physiologically active polypeptide is present in an amount of from 0.1 to 1% by weight.

10. The pharmaceutical composition of claim 1, wherein the physiologically active polypeptide is EPO.

11. The pharmaceutical composition of claim 1, wherein A has a molecular weight of 2,000 to 150,000 Daltons.

12. The pharmaceutical composition of claim 1, wherein B has a molecular weight of 1,000 to 15,000 Daltons.

13. The pharmaceutical composition of claim 1, wherein the ABA triblock copolymer has a molecular weight of 5,000 to 50,000 Daltons.

14. The pharmaceutical composition of claim 1, wherein the polyethylene glycol is present in an amount of from 20 to 50 mol % relative to the total amount of ABA triblock copolymer.

15. The pharmaceutical composition of claim 1, wherein the lactic acid is present in an amount of from 40 to 60 mol % relative to the total amount of ABA triblock copolymer.

16. The pharmaceutical composition of claim 1, wherein the glycolic acid is present in an amount of from 5 to 25 mol % relative to the total amount of ABA triblock copolymer.

17. The pharmaceutical composition of claim 1, wherein the lactic acid and the glycolic acid are present in a ratio of 1:1 to 5:1.

18. The pharmaceutical composition of claim 1, wherein the lactic acid and the glycolic acid are present in a ratio of about 2:1 to 4:1.

19. The pharmaceutical composition of claim 1, wherein the additive is present in an amount of from 0.5 to 40% by weight.

20. The pharmaceutical composition of claim 1, wherein the additive comprises a disaccharide or dextran having a molecular weight of 20,000 to 60,000 Daltons, which is present in an amount of from 5 to 15% by weight.

21. The pharmaceutical composition of claim 1, wherein the additive comprises dextran having a molecular weight of 20,000 to 60,000 Daltons.

22. The pharmaceutical composition of claim 21, wherein the additive further comprises poly-L-arginine or poly-L-histidine.

23. A process for producing a pharmaceutical composition comprising microparticles of a biodegradable polymer matrix in which a physiologically active polypeptide having a nonzero degree of loading of up to about 3% is embedded, the process comprising:

(a) dissolving an ABA triblock copolymer in an organic, water-immiscible solvent to form a dissolved ABA triblock copolymer, wherein A represents a copolymer of lactic acid and glycolic acid and B represents a polyethylene glycol chain, (b) dispersing the dissolved ABA triblock copolymer with a solution or suspension of a physiologically active polypeptide to produce a first emulsion, wherein the solution or suspension contains an additive comprising at least one member selected from the group consisting of (1) a disaccharide, (2) dextran having a molecular weight of 20,000 to 60,000 Daltons, (3) an amino sugar, (4) an amino acid, (5) a detergent, (6) a mixture of dextran having a molecular weight of 20,000 to 60,000 Daltons and a cyclodextrin or derivative thereof, (7) a mixture of dextran having a molecular weight of 20,000 to 60,000 Daltons and a polyamino acid, and (8) a mixture of dextran having a molecular weight of 20,000 to 60,000 Daltons and an amino acid;

(c) dispersing the first emulsion in an aqueous solution containing a stabilizer to produce a second emulsion;

(d) evaporating the organic solvent to produce microparticles; and (e) thereafter isolating the microparticles.

wherein the additive is contained in the pharmaceutical composition in an mount of 1 to 20% by weight in relation to the total weight of the microparticles and the additive substantially prevents aggregation of the physiologically active polypeptide and provides a lower rate of release of the physiologically active polypeptide from the microparticle than a corresponding pharmecuetical composition without the additive.

24. The process of claim 23, wherein, in step (b), the dissolved ABA triblock copolymer is subjected to a dispersal period of 30 seconds.

25. The process of claim 23, wherein, in step (b), the dissolved ABA triblock copolymer is subjected to two dispersal periods of 30 seconds each, with an interval of 30 seconds between the two dispersal periods.

26. The process of claim 23, wherein the process is conducted at a temperature of 0 to 6° C.

27. The process of claim 23, wherein the aqueous solution and the organic solvent are present in a weight ratio of up to 20 to 25%.

28. A pharmaceutical composition produced by the process of claim 23.

* * * * *